(12) United States Patent
Coleman et al.

(10) Patent No.: US 6,472,163 B1
(45) Date of Patent: *Oct. 29, 2002

(54) SOLID PHASE ENZYME KINETICS SCREENING IN MICROCOLONIES

(75) Inventors: William J. Coleman, Mountain View; Edward J. Bylina; Douglas C. Youvan, both of San Jose, all of CA (US)

(73) Assignee: Kairos Scientific, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/520,106

(22) Filed: Mar. 7, 2000

Related U.S. Application Data

(63) Continuation-in-part of application No. 09/309,189, filed on May 10, 1999, now abandoned, which is a continuation of application No. 09/098,202, filed on Jun. 16, 1998, now Pat. No. 5,914,245.
(60) Provisional application No. 60/082,440, filed on Apr. 20, 1998.

(51) Int. Cl.[7] .............................. C12Q 1/44; C12Q 1/37; C12Q 1/48
(52) U.S. Cl. .............................. 435/19; 435/23; 435/24; 435/15; 435/25; 435/4; 435/808; 435/283.1; 435/968; 422/50
(58) Field of Search .............................. 435/19, 23, 24, 435/14, 15, 25, 4, 808, 283.1, 968; 422/50

(56) References Cited

U.S. PATENT DOCUMENTS 5,914,245 A * 6/1999 Bylina et al. .................. 435/19

FOREIGN PATENT DOCUMENTS

| EP | 0 496 345 A1 | 7/1992 |
|---|---|---|
| WO | WO 99/35496 | 7/1999 |

OTHER PUBLICATIONS

Advertisement entitled "Evolve into something powerful," *Nature biotechnology*, 17(4), Apr. 1999.
Advertisement entitled "Evolve into something powerful," *Chemical*, Oct. 19, 1998.
Advertisement entitled "Evolve into something powerful," *Chemical & Engineering News*, Mar. 29, 1999.
Boardman, et al., "Automated Spectral Analysis: A Geological Example Using Aviris Data, North Grapevine Mountains, Nevada," Proceedings of the Tenth Thematic Conference re Geologic Remote Sensing, vol. 1, May 9–12, 1994, San Antonio, TX, pp. I–407–I418.
Cover Figure, *Current Opinion in Microbiology*, 2(3), Jun. 1999.
Fox, Jeffrey L., "Hercules and Kairos catalyze enzyme deal,", *Nature Biotechnology*, 17(5), p. 417, May 1999.
Green, Andrew, et al., "A Transformation for Ordering Multispectral Data in Terms of Image Quality with Implications for Noise Removal," IEEE Transactions on Geoscience and Remote Sensing, vol. 26, No. 1, Jan. 1988, pp. 65–74.

(List continued on next page.)

Primary Examiner—Louise N. Leary
(74) Attorney, Agent, or Firm—Bingham Mccutchen LLP; Michael J. Shuster

(57) ABSTRACT

Improvements in calorimetric assays, surfaces for arraying microcolonies and instrument hardware for screening mutagenized enzymes and proteins in a solid phase format are presented. These improvements permit new enzyme activities to be screened. New filter membrane materials and formats for arraying the microcolonies provide higher throughput, better solvent resistance and ease of handling. Modifications to the instrument heating and illumination systems provide improved temperature control and a more compact, folded light path.

175 Claims, 1 Drawing Sheet

OTHER PUBLICATIONS

Hercules Incorporated News Release, Hercules Establishes Partnership with Kairos Scientific, 99–5–C, Mar. 10, 1999.

"Hercules licenses Kairos biocatalysis technology," *Chemical & Engineering News*, p. 12, Mar. 22, 1999.

International Search Report, mailed Feb. 8, 2002, corresponding PCT US/01/02180.

"Kairos' kCAT Service" web posting to Kairos Scientific web page on Aug. 4, 1998.

"News—Collaborations & Agreements," *Genetic Engineering News*, 19(7), Apr. 1, 1999.

Reisch, Marc S., "A Modern–Day Hercules Bulks Up," *Chemical Engineering News*, pp. 13–15, Apr. 5, 1999.

Written Opinion, mailed Jun. 26, 2001, International Application No. PCT US/99/13824.

Yahoo Finance Web Site Press Release "Hercules Establishes Partnership with Kairos Scientific," Mar. 12, 1999.

Yang, M.M., et al., "Applications of Imaging Spectroscopy in Molecular Biology: I. Screening Photosynthetic Bacteria," *Biotechnology*, 6:8, (Aug. 1988), pp. 939–942.

Yang, M.M., et al., "High Resolution Imaging Microscope (HIRIM)", *Biotechnology et alia*, ISSN 1532–5474 (1998) 4:1–20, XP002186904.

Yang, M.M., et al., "Graphical User Interface for single–pixel spectroscopy," *Biotechnology et alia*, ISSN 1532–5474 (Sep. 08, 2000) 5:1–8, XP002186905.

Youvan, Douglas C., "Imaging Spectroscopy and Solid Phase Screening," IBC World Congress on Enzyme Technologies, Mar. 10–12, 1999, San Francisco, California.

Caldwell et al., "Imaging of Bacterial Cells by Fluorescence Exclusion Using Scanning Confocal Laser Microscopy," *J. Microbiological Methods*; vol. 15(4), pp. 249–261, (1992) (Abstract).

Weaver et al., "A General Method for Separating Cells by Function and Composition," *Methods (San Diego*, vol. 2(3), pp. 234–247, (1991) (Abstract).

* cited by examiner

SOLID PHASE ENZYME KINETICS SCREENING IN MICROCOLONIES

CROSS-REFERENCE TO RELATED APPLICATIONS

This application is a continuation-in-part of U.S. application Ser. No. 09/309,189, filed May 10, 1999 (abandoned), which is a continuation of U.S. application Ser. No 09/098,202, filed Jun. 16, 1998, now U.S. Pat. No. 5,914,245, which claims the benefit of U.S. Provisional Application No. 60/082,440, filed Apr. 20. 1998 (abandoned).

STATEMENT AS TO FEDERALLY SPONSORED RESEARCH

This invention was made with Government support, awarded by the National Institutes of Health. The Government may have certain rights in the invention.

TECHNICAL FIELD

The invention relates generally to enzymes, and specifically to solid phase enzyme kinetics screening in microcolonies of biological cells.

BACKGROUND OF THE INVENTION

Demand for New Enzyme Activities

Enzymes are increasingly being used as catalysts in industry, agriculture, medicine and scientific research. Due to their substrate specificity, chemical selectivity and environmental compatibility, enzymes offer advantages for such applications as the synthesis of chirally pure pharmaceuticals, textile processing, food processing, medical diagnostics and therapy, biotransformation and bioremediation (Ogawa & Shimizu, 1999; Marrs et al., 1999; Bull et al., 1999). Enzymes are proving to be superior to traditional chemical processes for modifying high molecular weight polymers (Akkara et al., 1999). A review of enzymes as biocatalysts and their incorporation into industrial processes can be found in Uhlig et a. (1998).

Although many wild-type enzymes (i.e., those whose amino acid sequences are the same as those found in naturally occurring organisms) can be used without any modification, there are many instances wherein the physical properties of an enzyme or its chemical activity are not compatible with a desired application. Novel physical properties which might be desirable could include, for example, thermal stability, resistance to non-aqueous solvents, salt, metals, inhibitors, proteases, extremes of pH and the like. Reducing the size of the enzyme, abolishing its dependence on cofactors or other proteins, improving its expression in the host strain and other similar changes might also be desirable for a particular application. Improved chemical activities might include, for example, enhanced catalytic rate, substrate affinity and specificity, regioselectivity, enantioselectivity, reduced product inhibition, or an altered pH-activity profile. In addition, it may be desirable to alter the properties of one or more enzymes that function together as part of a metabolic pathway (Nielsen, 1998; Hutchinson, 1998; Jacobsen & Khosla, 1998).

Mutagenesis Techniques for Improving Enzymes

Mutations that encode amino acid changes can be useful for generating novel enzyme activities. The genes can be obtained using any method known to one of skill in the art, e.g. by isolating clones from a genomic library of a given organism, by polymerase chain reaction (PCR) amplification from a source of genomic DNA or mRNA, or from a library of expression clones from a heterogeneous mixture of DNA from uncultivated environmental microbes (U.S. Pat. No. 5,958,672). There are numerous methods that are well known to those skilled in the art for mutating the genes encoding enzymes and other non-catalytic proteins and peptides. These methods include both rational (e.g., creating point mutants or groups of point mutants by site-directed mutagenesis) and stochastic (e.g., random mutagenesis, combinatorial mutagenesis and recombination) techniques. One embodiment of rational design, termed protein design automation, uses an algorithm to objectively predict protein sequences likely to achieve a desired fold. Stabilized protein sequences can be designed by combining potential functions that model a protein sequence's compatibility with a desired structure, and fast optimization tools that can search the enormous, number of sequence possibilities that occur in sequence space (Dahiyat & Mayo, 1996; Dahiyat et al., 1997; Dahiyat, 1999; Pat. Application No. WO 98/47089). In one embodiment, this method of quantitative protein design and automation can be used to search sequence space to pre-screen enormous sequence libraries, thereby reducing the size of the library that must be experimentally screened. Stochastic methods include, for example, chemical mutagenesis (Singer & Kusmierek, 1982), recursive ensemble mutagenesis (Arkin & Youvan, 1992; Delagrave et al., 1993), exponential ensemble mutagenesis (Delagrave & Youvan, 1993), sequential random mutagenesis (Chen & Arnold, 1991; 1993), DNA shuffling (Stemmer, 1994a,b) and the like. These techniques may be used individually or in combination to produce mutations. However, because the mutations are produced randomly or semi-randomly, a selection or screen must be used to identify which clones contain desirable mutations.

The stochastic methods can be used to generate an ensemble or library of mutated genes that have been cloned into plasmids or other vectors, wherein each copy of the gene may have a different sequence. The mutagenized library may contain up to $10^7$ or more different members, and is therefore often. referred to as a high-complexity library. Generating a high complexity library is essential if a desirable mutation or class of mutations is represented at. a very low frequency within the population. When all or part of the library containing the mutated genes is expressed in an appropriate host organism (e.g., *E. coil*), the expressed enzyme activity can be assayed, and the clones containing the desired activity can be purified. DNA encoding the desired enzyme or protein can then be isolated from this expression library and sequenced. By repeating the steps of mutagenesis and screening, novel enzymes and other proteins can be artificially created. This iterative process is known as directed evolution. The genes of interest do not necessarily have to be expressed on plasmids. They can also be expressed following integration into the host chromosome or as a result of mutating the chromosomal copy of a gene. Note also that high complexity expression libraries can be created without mutagenesis. This can be done by cloning and expressing DNA from a source that already contains a large number of different sequences, such as highly heterogeneous genomic DNA from a mixture of environmental microbes.

Activity Screening of Expression Libraries

Screening for the desired biological activity can be done by contacting the host cells expressing the enzyme with a chromogenic or fluorogenic compound that is appropriate for the enzyme reaction and monitoring the formation of color in the cells or their surroundings. In the solid-phase assays described in U.S. Pat. No. 5,914,245, these compounds are referred to as optical signal substrates because they produce a measurable change in absorbance, reflectance, fluorescence or luminescence when they come in contact with active enzyme or with a product of the enzymatic reaction. These substrates can be obtained from a variety of suppliers, including Molecular Probes (Eugene, Oreg.), Sigma-Aldrich (St. Louis, Mo.), Biosynth (Naperville, Ill.), Research Organics (Cleveland, Ohio), CarboMer (Westborough, Mass.) and Megazyme (Wicklow, Ireland). For liquid phase assays, activity screening can be done, for example, by picking individual colonies from a growth plate, transferring each colony to an appropriate buffer solution in the well of a microplate, adding a chromogenic or fluorogenic substrate, and monitoring the change in absorbance or fluorescence with a microplate reader. An example of this method can be found in Moore & Arnold (1996). For solid phase assays, which are described in U.S. Pat. No. 5,914,245, the colonies can be maintained on a substantially continuous base, such as a microporous polymeric membrane filter, during the steps of deposition, growth, induction, lysis and assay. Microporous membranes contain numerous randomly distributed pores having a diameter of less than about 20 micrometers, and typically less than about 1 micrometer.

U.S. Pat. No. 5,914,245 also describes why it is advantageous to use microcolonies instead of colonies for screening biological activity. A microcolony is a clump of cells that are clonally derived from a single parent cell. A microcolony differs from a colony in that a colony is visible to the naked eye, whereas a microcolony need not be visible. A microcolony can be composed of any biological cells, including those from the domains Archaea, Bacteria or Eucarya. Note, however, that in addition to microcolonies, the solid-phase technique can also be used to screen phage plaques. Advantages of solid phase screening include ease of handling and reduced substrate usage. Advantages of using microcolonies versus colonies for this purpose include improved uniformity of color development across each colony and higher overall throughput per assay.

Screening Using the MicroColonyImager (MCI)

KAIROS has developed the MicroColonyImager (MCI) in conjunction with a colorimetric solid phase assay system to screen libraries expressing mutagenized enzymes or other proteins for enhanced biological activity. Using microcolonies grown at a nearly confluent density of 50,000 colonies per assay disk, this high-throughput system: (a) obtains high-resolution spectral data and makes kinetic measurements on each microcolony on the assay disk, (b) requires less than 100 nanoliters of substrate per assayed microcolony, and (c) detects as little as a two-fold difference in enzyme rates among microcolonies. The instrument can be used in conjunction with various chromogenic, fluorogenic, lumigenic and fluorescence resonance energy transfer (FRET) substrates to measure biological activity. We have previously demonstrated, for example, that the MCI technology can be used in multiplexed assays to distinguish microcolonies that show a preference for hydrolyzing the substrate Red-gal (6-Chloro-3-indolyl-Beta-D-galactopyranoside) over its epimer, X-glu (5-Bromo-4-chloro-3-indolyl-Beta-D-glucopyranoside). A description of the MCI device and methods for employing the device for solid-phase screening, as well as examples of the MCI graphical user interface can be found in U.S. Pat. No. 5,914,245.

As the need for large, highly complex mutagenized libraries increases, there is a concomitant need to develop better solid-phase screening technology to find desirable mutants. Accordingly, new methods and hardware are provided herein for accomplishing this end.

SUMMARY OF THE INVENTION

The present invention provides assay methods and membrane filter materials as well as hardware modifications for performing solid-phase enzyme screening in microcolonies of biological cells. These improvements make it easier to assay a wide variety of enzymes, provide assay membranes that have easier handling characteristics and chemical resistance, increase the overall throughput of the device, permit better temperature control of the reaction chamber and reduce the optical light path for the illumination system.

The present invention provides a means to improve methods for imaging and analyzing microcolonies of cells, for performing solid-phase directed evolution enzyme screening, and for performing solid-phase enzyme discovery screening. These methods are improved by incorporating additional solid-phase assays, including direct and indirect assays using indicators, coupled assays using indicators and indicator enzymes, coupled assays wherein the enzyme being screened produces a reaction product that is not a substrate for the indicator enzyme, inhibitor desensitization assays, and assays for screening enzymes that synthesize, modify or depolymerize high molecular weight substrates. In particular, additional types of optical signal substrates are described for use in microcolony screening, as well as methods for incorporating them into high-throughput solid-phase assays. Many of these assays are useful for screening enzymes that transform high-molecular weight substrates. Such enzymes are difficult to assay without using the solid-phase format. The improvements described in the present invention permit the user to more easily screen these enzyme activities in a high-density solid-phase format.

The present invention also incorporates additional polymer compositions for the substantially continuous base or membrane which is used to hold the microcolonies. Additional materials for the wick, which supplies optical signal substrate to the microcolonies, are also described. Microporous polyester membranes, for example, were found to provide better membrane handling characteristics and resistance to warping, particularly in the presence of non-aqueous solvents. There was also a need to expand the size of the substantially continuous base for each assay so that more microcolonies can be simultaneously measured. Increasing the size of the assay membrane to occupy more of the viewable area of the device improves the overall throughput for each assay. The original paper wick can be replaced by a hydrated gel comprising a polymer, such as agarose or polyacrylamide, in addition to the substrate. This provides highly uniform contact between the microcolonies and the substrate.

The invention further provides improvements to the illumination systems and temperature control of the MicroColonyImager. The light path and overall size of the instrument can be reduced by replacing the integrating sphere with a glass diffuser. More uniform heating of the sample compartment can be achieved by incorporating an electrical heater and a temperature feedback circuit. The present invention also describes additional types of detectors that can be used with the MCI system.

DETAILED DESCRIPTION OF THE INVENTION

Figure 1:
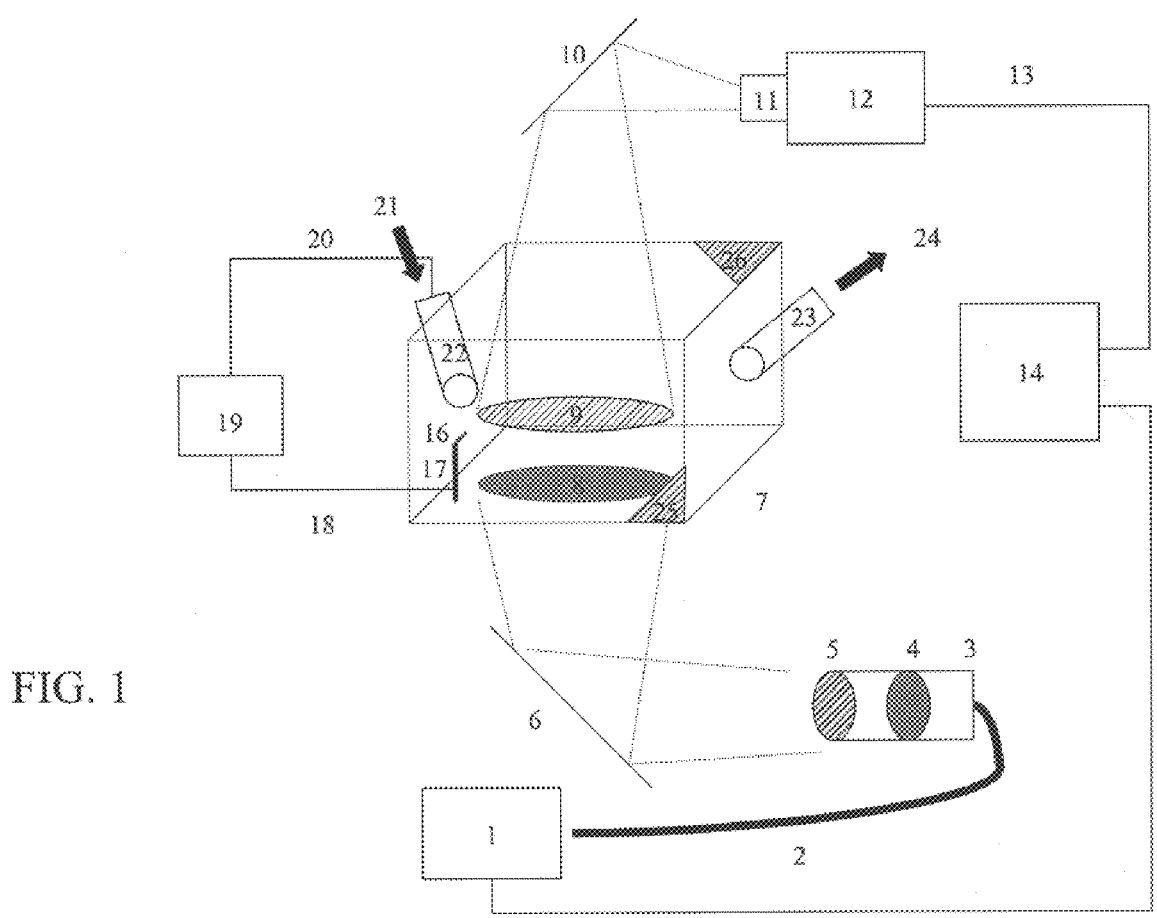
FIG. 1. is a depiction of the improved MicrocolonyImager with a compact light path and a temperature-controlled sample chamber.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and material are described below.

Other features and advantages of the invention will be apparent from the following detailed description, the drawings, and from the claims.

Microcolony Assays

Additional types of solid-phase assays using optical signal substrates can be applied to screening biological activity in microcolonies. These include: (1) direct or indirect assays using various indicators, (2) coupled assays using at least one additional indicator enzyme and at least one additional indicator, (3) coupled assays that rely on activation or deactivation of a compound that is not a substrate for an indicator enzyme (e.g., an inhibitor of the indicator enzyme), (4) inhibitor desensitization assays, and (5) assays employing substrates that comprise high molecular weight polymers.

(1) Indicator compounds can be used to detect one or more products of an enzymatic reaction by interacting either directly or indirectly with the products. In one embodiment, these indicator compounds can be included as part of the optical signal substrate solution. For example, U.S. Pat. No. 5,914,245 describes a lipase assay that detects fatty acid interactions with the fluorescent dye Rhodamine B. Other assays that can utilize indicator compounds include those wherein protons are generated or wherein transmembrane proton, electron or ion transfer occurs during an enzymatic reaction. These activities can be detected in microcolonies by including various dyes in the substrate solution. Fluorescent indicator dyes that can be used to monitor pH changes include fluorescein and seminaphthorhodafluors and their derivatives for the pH range 6–9 and LysoSensor, Oregon Green and Rhodol and their derivatives for the pH range 3–7. These fluorescent pH indicators are available from Molecular Probes (Eugene, Oreg.). Chromophore dyes whose wavelength of maximum absorption changes as a function of pH include Thymol Blue (approximate useful pH range 1.2–2.8 and 8.0–9.6), Methyl Orange (pH 3.2–4.4), Bromocresol Green (pH 3.8–5.4), Methyl Red (pH 4.2–6.2), Bromothymol Blue (pH 6.0–7.6) and Phenol Red (pH 6.8–8.2). Phenolphthalein (pH 8.2–10.0) turns from colorless to pink as the pH becomes more alkaline. These colorimetric pH indicators are available from Sigma-Aldrich (St. Louis, Mo.). There are numerous examples in enzymology of using pH indicators for detecting enzymatic activity (Wajzer, 1949; Darrow & Colowick, 1962; Crane & Sols, 1960; Lowry et al., 1951; Khalifah, 1971; Rosenberg et al., 1989; Whittaker et al., 1994). Indicators such as Bromothymol Blue and Phenol Red have been used to assay the activity of various hydrolases in solution (Moris-Varas et al., 1999).

Hydrolase activity within a microcolony can release protons during the enzymatic reaction. Thus, many hydrolases such as esterases, lipases, amidases, hydantoinases and proteases, can be assayed in solid phase by using the appropriate indicator and monitoring the decrease in pH over time. The direct interaction between the released proton and the indicator molecule changes the chemical and electronic structure of the indicator such that its optical absorption properties also change. Thus, for example, the activity of a lipase expressed in a microcolony can be assayed by contacting the microcolonies with a substrate solution containing 20 mM potassium phosphate buffer at pH 7.2, about 15 mM of an enantiomerically pure ester (e.g., (R)-Methyl mandelate) and 0.001% Bromothymol Blue indicator. The buffer concentration is set just low enough to allow the lipase-catalyzed production of the mandelic acid product to overcome the buffering capacity of the phosphate buffer and lower the pH. The kinetics of the reaction in the microcolonies are monitored at 430 nm and 615 nm. Microcolonies expressing active enzyme variants convert the yellow indicator (absorbing maximally at about 430 nm) to a blue indicator (absorbing maximally at about 615 nm) as the pH drops below about 7.2. The rate of change of the indicator is proportional to the amount of ester being cleaved. These indicators have been shown to be useful for assaying the activity of purified lipases in solution (Moris-Varas et al., 1999) and lipases expressed in bacterial colonies on agar growth medium (Bornscheuer et al., 1999), but the technique has not been applied to enzymes expressed by synchronous induction in microcolonies on solid phase, wherein the change in the optical signal due to enzyme activity is automatically monitored over time.

Indicators can also be used to monitor the distribution of inorganic ions across cell membranes as well as the redox state of the microcolonies. Thus, enzymes such as ion channels, transmembrane transporters or oxidoreductases can be assayed. The interaction of the indicator dye with the reaction product can be either direct or indirect. The assayed products comprise electrons or small ions (such as sodium, potassium, chloride, calcium or reactive oxygen). Intracellular calcium can be measured by numerous fluorescent dyes that directly bind the metal ion (Takahashi et al., 1999). Examples of these indicators are the UV-excitable dyes Fura-2 and Indo-1 from Molecular Probes (Eugene, Oreg.). Fura-2 can be monitored by measuring the fluorescence emission at about 510 nm while measuring the fluorescence excitation between 300 and 400 nm. Binding of calcium to the indicator dye creates a shift in the absorption spectrum of the fluorophore that can be detected by ratio imaging. Binding of calcium to Indo-1 can be determined by exciting the microcolonies containing the fluorophore at about 340 nm and monitoring the shift in the maximum wavelength for fluorescence emission from about 475 nm in the absence of calcium to about 400 nm when the fluorophore is completely saturated. The intracellular and extracellular concentration of ions such as sodium and potassium is controlled by membrane transporters, and can be measured with fluorescent benzofuranyl crown ethers and their cell-permeant acetoxymethyl ester derivatives. These dyes exhibit a change in their fluorescence properties when they directly bind the ions. As the sodium concentration increases, the sodium-sensitive dye SBFI (Molecular Probes; Eugene, Oreg.) shows a concentration-dependent increase in quantum yield, as measured by the increase in fluorescence emission at 505 nm when excited at 340 or 380 nm. Similarly, the potassium-sensitive dye PBFI, also available from Molecular Probes, shows an increase in the quantum yield of fluorescence emission at 505 nm when excited at 340 or 380 nm. The fluorescence emission of the chloride-sensitive indicators MQAA and MQAE (Molecular Probes; Eugene, Oreg.) is collisionally quenched as the chloride concentration increases. The chloride-sensing dyes can be excited at about 350 nm and the fluorescence emission is monitored at 445–460 nm. All of these ion-sensing indicators can thus be used to monitor the activity of ion transport across cell membranes.

The activity of electron transfer enzymes can be monitored by measuring the fluorescence or absorption of redox-active indicator dyes that act as electron acceptors. In this case, electrons are tranferred directly to the dye. Reduction of the dye causes a change in its electronic structure, which can be measured. For example, reduction of resazurin at pH greater than about 9.0 converts the molecule to a highly fluorescent form that can be detected at about 580 nm. This change in emission intensity can be used to assay oxidative activity within microcolonies. The electron-accepting chromophore 2,6-Dichlorophenolindophenol (DCIP) is transformed by reduction to a colorless form. At pH 7.2, the loss of absorbance at about 600 nm can be used to monitor the kinetics of electron transfer through electron transfer complexes. Other non-fluorescent indicator compounds such as dihydrofluorescein and dihydrorhodamine derivatives are oxidized by reactive oxygen species to create fluorescent products. The production of these fluorescent products indicates oxidative activity within the microcolonies.

There are also fluorescent redox-sensitive indicators that can be used to indirectly sense the transmembrane redox potential in cells. These potentiometric indicator dyes, which respond to the gradient of ions across a cell membrane, include aminonaphthylethenylpyridinium (ANEP), carbocyanine and oxonol dyes, and are available from Molecular Probes (Eugene, Oreg.). ANEP, for example, is maximally excited at 496 nm and emits maximally in the near-infrared at about 705 nm. Its emission intensity decreases as-the membrane becomes hyperpolarized. The carbocyanine dye $DiSC_3$ is maximally excited at 651 nm and emits fluorescence at 675 nm. Its fluorescence emission is quenched by the development of a transmembrane potential. Oxonol dyes can be excited between 490 nm and 610, depending on the derivative, and emit fluorescence between 516 and 640 nm. Their fluorescence emission also decreases in response to hyperpolarization of the membrane. These indirect indicators can be used to monitor the activity of membrane-bound ion pumps within the microcolonies.

Indicators can also be used to react directly with larger molecules that are the products of an enzymatic reaction. The reaction generates a color change that can be automatically optically monitored. For example, the activity of glycohydrolases that generate reducing sugars as a product can be assayed using the reagent 2,3,5-Triphenyl-2H-tetrazolium chloride (also known as TTC or TPTZ; Sigma-Aldrich; St. Louis, Mo.) at a final concentration of about 0.2 mM. TTC reacts with these sugars to produce an insoluble pink formazan product whose absorbance can be optically detected at about 480–485 nm. Another example of an assay that employs a reactive indicator involves screening for alkaline phosphatase, which hydrolyzes a naphthol phosphate ester substrate (Naphthol AS-MX from Pierce, Inc., Rockford, Ill.) to a reactive naphtholic compound and a free phosphate. The naphtholic compound can then react with a secondary compound, which is a diazonium salt (Fast Red TR Salt), to generate an intensely colored (red) azo dye precipitate.

(2) It is also possible to optically monitor an enzyme activity that does not by itself generate a colored or fluorescent product by coupling this activity to that of one or more enzymes and one or more additional indicators to ultimately generate an observable product. Moreover, even though the initial enzyme reaction may generate a colored product such as NADH or NADPH, it is sometimes desirable to couple this reaction to a second enzyme reaction that produces a more intensely colored, precipitating product, such as formazan. For example, there are numerous dehydrogenases that oxidize a substrate and simultaneously reduce $NAD^+$ to NADH. In cells that do not have diaphorase activity, the activity of the dehydrogenase can be measured in a coupled assay by adding to the assay medium, in addition to $NAD^+$ and the particular dehydrogenase substrate, purified diaphorase and the indicator Nitro Blue Tetrazolium (NBT, or 2,2'-Di-p-nitrophenyl-5,5'-diphenyl-3,3'[3,3'-dimethoxy-4,4'-diphenylene]-ditetrazolium chloride) or similar tetrazolium compounds. The diaphorase acts as an indicator enzyme by oxidizing the NADH and reducing the tetrazolium to form an intensely colored precipitate (Nachlas et al., 1960; Dona, 1985; Cristol et al., 1985) within the active microcolonies. The production of the tetrazolium product is thus mediated by the indicator enzyme, and the increase in the absorbance of the final tetrazolium product over time is proportional to the activity of the dehydrogenase enzyme. The absorbance of the precipitated NBT-formazan can be measured in the wavelength range between about 540 and 660 nm. The diaphorase is most active at a pH between about 7.5 and 9.4. Purified diaphorase is available from Worthington Biochemical Corporation (Lakewood, N.J.).

A second example of a coupled assay involves oxidase enzymes, such as glucose oxidase, L-amino acid oxidase, and the like. The activity of these enzymes generates $H_2O_2$ as a product. The kinetics of the enzyme with respect to hydrogen peroxide formation can be indirectly assayed by including peroxidase and a calorimetric indicator in the substrate solution. The peroxidase reduces the hydrogen peroxide to water and oxidizes the colorimetric indicator. Thus, the peroxidase acts as an indicator enzyme that mediates an indirect interaction (i.e., transfer of electrons) from the reaction product of the first enzyme and the colorimetric indicator. Examples of such colorimetric indicators that are useful for solid-phase enzyme screening include 4-Chloro-1-naphthol from Pierce (Rockford, Ill.), which generates a blue-purple precipitate, or TMB (3,3', 5,5'-Tetramethylbenzidine), which generates a blue product. Examples of peroxidases that can be used as indicator enzymes are horseradish peroxidase, soybean peroxidase, haloperoxidase (including both chloroperoxidase and bromoperoxidase), myeloperoxidase, cytochrome c peroxidase, tulip peroxidase, lignin peroxidase, carrot peroxidase, peanut peroxidase, and peroxidase Novozyme® 502. In the preferred embodiment, the indicator enzyme is horseradish peroxidase or soybean peroxidase. Soybean peroxidase has the advantage of being more resistant to thermal inactivation. This type of coupled assay can be extended to include three enzymes. For example, the activity of acetylcholinesterase, which generates choline as one of the products, can be assayed by using a combination of choline oxidase, peroxidase and an indicator dye. The choline oxidase oxidizes the choline to produce $H_2O_2$ as one of the products (along with betaine), and the peroxidase reduces the $H_2O_2$ and oxidizes 4-Chloro-1-naphthol at pH near 7, for example, to a colored precipitate. Formation of the precipitated product can be optically monitored at 550 nm.

Coupled assays utilizing peroxidases and laccases as indicator enzymes for evolving oxygenases have also been described (Joo et al., 1999; Pat. Application No. WO 99/60096). In these examples, an indicator peroxidase was either added to the substrate solution or co-expressed in the *E. coli* host; however, only the oxygenase or dioxygenase gene was mutagenized. This method can be used to evolve the gene encoding the *Pseudomonas putida* $P450_{cam}$ (a monooxygenase) according to the procedure described in Joo et al. (1999). In this method, the cells expressing the mutagenized P450 are exposed to naphthalene, monosubstituted benzene, or other aromatic compounds. The P450 hydroxylates the aromatic substrate. The indicator peroxidase then polymerizes the hydroxylated product in the presence of hydrogen peroxide to form a fluorescent polymer, which can be detected. This type of assay can be used to screen a number of enzymatic activities, including chloroperoxidase, cytochrome P450, methane monooxygenase, toluene monooxygenase, toluene dioxygenase, biphenyl dioxygenase and naphthalene dioxygenase. Reactants that can be used in the assay include naphthalene, 3-phenylpropionate, benzene, toluene, benzoic acid, anthracene, benzphetamine or coumarin. Peroxidases that can be used as indicator enzymes for the assay include horseradish peroxidase, cytochrome c peroxidase, tulip peroxidase, lignin peroxidase, carrot peroxidase, peanut peroxidase, soybean peroxidase, and peroxidase Novozyme® 502. Laccase, which uses molecular oxygen as a substrate instead of peroxide, can also be used as the indicator enzyme. The methods described in Joo et al. (1999) and in Pat. Application No. WO 99/60096 provide a means to screen colonies expressing these oxygenases, but unlike in the method of solid-phase screening performed by the MicroColonyImager, the other methods do not automatically optically monitor the colonies over time for changes in the optical signal of the colonies. This feature of the MicroColonyImager is useful, for example, in detecting microcolonies expressing undesirable enzyme variants that display product inhibition. The combined kinetic and spectral acquisition capabilities of the MicroColonyImager also make it possible to distinguish various oxygenase activities with different regiospecificities, since the UV-visible absorption and fluorescence properties of the different hydroxylated products created by peroxidase-catalyzed polymerization reaction can be quite distinct.

(3) A third type of assay that can be employed for solid phase screening is a coupled assay wherein the enzyme being screened produces a reaction product that is not a substrate for the indicator enzyme. For example, microcolonies expressing an enzyme that modifies the drug acarbose (an inhibitor of alpha-glucosidase) can be indirectly assayed by including the following compounds in the substrate solution: acarbose (Bayer, Inc; Pittsburgh, Pa.), purified alpha-glucosidase as the indicator enzyme, and 5-Bromo-4-chloro-3-indolyl-alpha-D-glucoside as the indicator (Sigma-Aldrich; St. Louis, Mo.). In the absence of inhibitor, alpha-glucosidase hydrolyzes the indolyl derivative to produce an intensely colored indigo precipitate. Galactose oxidase and glucose oxidase are examples of enzymes that can be mutagenized so that they are capable of chemically modifying the glucose moieties in acarbose. If a variant of the modifying enzyme does not alter the structure of the acarbose, or if it produces another inhibitory form of acarbose, this is indicated by low rates of alpha-glucosidase activity (i.e., lower rates of indigo formation). However, if an enzyme variant expressed in a microcolony modifies acarbose so that it is not inhibitory to the alpha-glucosidase indicator enzyme, the microcolony displays enhanced color formation. The kinetics of formation of the indigo product can be measured at 610 nm. This type of assay can be used to screen for new enzyme activities that are useful for developing, synthesizing and detoxifying drugs.

(4) A fourth type of solid phase assay is designed to evolve an enzyme so that it is desensitized to a particular inhibitor. This can be done using an assay wherein the signal arises from an interaction between the reaction product and an indicator. This approach may be desirable for modifying the sequence of an existing enzyme so that it is resistant to a particular inhibitor, or to discover an enzyme that is naturally resistant. For example, the lipase secreted from *Pseudomonas aeruginosa* is inhibited by the serine-specific inhibitor diethyl-p-nitrophenylphosphate (Jaeger et al., 1992). By including the inhibitor in the substrate solution that is added to the microcolonies (in addition to the ester substrate, the pH indicator dye and the buffer), it is possible to screen for new enzyme variants that are unaffected or less affected by the inhibitor. When the gene for the inhibitor-resistant enzyme is transferred to a plant species by incorporation into the plant chromosome, the inhibitor can then be used as a herbicide to suppress the growth of other plants that do not possess the altered gene. An example of the usefulness of this approach is presented in U.S. Pat. No. 5,290,926, which describes methods to select for variants of the enzyme histidyl dehydrogenase that are resistant to herbicide inhibitors. Such enzyme variants are useful for producing transgenic crop plants that are metabolically resistant to a given herbicide. Solid-phase screening in microcolonies can be used to find inhibitor-resistant enzyme variants in cases where selective growth cannot be employed.

(5) A fifth type of solid phase assay involves screening enzymes that synthesize, modify or depolymerize high molecular weight substrates. These substrates include polymers such as starch, cellulose, chitin, xylan, pectin, guar, protein and nucleic acids. High molecular weight substrates are defined herein as having a molecular weight greater than about 1,000 daltons. An advantage of using the MicrocolonyImager for assays involving high molecular weight compounds is that it is relatively easy to bring the porous membrane containing microcolonies and their enzyme variants in contact with the substrate. Since many of these polymers form gels or highly viscous solutions at room temperature, the paper wick soaked in substrate solution described in U.S. Pat. No. 5,914,245 can, in one embodiment, be replaced by a thin film of the polymer solution or gel. Alternatively, a thin film of agarose or other gel material mixed with the high molecular weight substrate or substrates can be used as a combination wick and substrate. The filter membrane containing the microcolonies can then be laid directly onto the wick to start the reaction. This procedure can be extended to more complex wicks, such as paper disks, dyed fabric, inked paper, and the like, which only require wetting with enough buffer to completely dampen the material before the microcolony filter membrane is laid down onto it. A solid-phase assay is highly advantageous for screening enzymes designed for paper or textile applications, such as de-inking of paper or textile finishing, because the assay can be performed directly on the intended target material.

There are numerous commercially available polymer substrates that are available for automatically optically monitoring the enzyme activity. These polymers can be dyed covalently or non-covalently, and the dye can be either a chromophore or fluorophore. Suppliers of dyed substrate compounds include Megazyme Inc. (Wicklow, Ireland), CarboMer Inc. (Westborough, Mass.), Sigma-Aldrich (St. Louis, Mo.), Fluka (Milwaukee, Wis.) and Molecular Probes (Eugene, Oreg.). Hydrolase activity can be detected by the presence of a clearing zone within and underneath the microcolony as the dye molecules are released from the polymer matrix and diffuse away from the center of the microcolony. Examples of chromophore-labeled high-molecular weight substrates are hydroxyethylcellulose dyed with Ostazin Brilliant Red H-3B for cellulase assays and 4-O-methyl-D-glucurono-D-xylan dyed with Remazol brilliant Blue R for xylanase assays. Both substrates are available from Fluka (Milwaukee, Wis.). In some cases, there may be slight shifts in the spectrum of the released dye molecules relative to the bound dye. It is also possible to use fluorescently labeled polymers, such as the EnzChek™ protease substrate from Molecular Probes (Eugene, Oreg.). This substrate contains a derivative of casein that is heavily labeled with either BODIPY FL or BODIPY TR-X, such that the fluorescence emission of the intact substrate is quenched. The fluorescence emission becomes unquenched when the polymer is hydrolyzed, and thus the activity of the enzyme can be determined in microcolonies by optically monitoring the increase in fluorescence intensity. BODIPY FL can be excited at 505 nm and emits at 513 nm. BODIPY TR-X can be excited at 589 and emits at 617 nm.

Cellulase activity in microcolonies can also be visualized using a substrate/enzyme kit manufactured by Molecular Probes (Eugene, Oreg.). Although the kit is designed for liquid-phase assays, it can also be adapted for use in solid-phase screening. The assay monitors cellulase activity by a coupled reaction using an indicator enzyme and a fluorescent indicator. Glucose produced by the cellulase activity is oxidized by glucose oxidase into gluconolactone and $H_2O_2$. In the presence of horseradish peroxidase, the reagent Amplex Red (a resorufin derivative) is transformed into fluorescent resorufin. The resorufin can be excited at 563 nm and emits fluorescence at 587 nm.

The activity of oxidative enzymes such as oxidases, oxygenases, dioxygenases, laccases, and peroxidases (including haloperoxidases, such as chloroperoxidase and bromoperoxidase) can also be assayed on colored polymers by monitoring the increase or decrease in absorbance as well as any spectral shifts. Spectral shifts can result from hydroxylation of the aromatic rings that comprise the dye. The hydroxylation reactions catalyzed by oxygenases are often regioselective. Ring-opening reactions due to the addition of dioxygen may cause loss of visible absorption. Crosslinking of dye molecules may create spectral shifts or generate fluorescent products. The action of these oxidative enzymes on aromatic dyes contained in inked or colored paper and dyed fabric or plastics can also be assayed directly on the colored material.

Secondary indicators can also be used to monitor enzyme activity with these substrates. For example, the activity of an oxidase for modifying alcohol groups on a polymer can be monitored in a coupled assay using soybean peroxidase as an indicator enzyme and 4-Chloro-1-naphthol as the chromogenic indicator to measure the $H_2O_2$ that is co-generated by the oxidase.

New Polymer Compositions for the Substantially Continuous Base

The present invention provides a new membrane material made of polyester for the substantially continuous base that holds the microcolonies. The 47 mm diameter/0.2 $\mu$m pore size polycarbonate disks (Poretics Products) used as assay disks in the high throughput solid-phase screening techniques described in U.S. Pat. No. 5,914,245 are microporous membranes, specifically track-etch membranes. A review of the properties of the Poretics® track-etch membranes described herein can be found in the Osmonics Poretics Products Catalog (1997–1998 ed.). Track-etching refers to the physical and chemical process by which the membranes are manufactured. The pores are created in thin sheets of membrane material by exposing the material to a collimated beam of high-energy charged particles, which leave behind sensitized tracks. These tracks are preferentially etched or dissolved into uniform cylindrical pores by subsequent exposure to a strong alkaline solution. Due to the fact that the pores in track-etch membranes are created by particle bombardment, they are non-tortuous, that is, they penetrate the membrane in a straight line. Track-etch membranes are available from a variety of suppliers [for example, SPI-Pore™ brands (from SPI Supplies, West Chester, Pa.), Cyclopore™ brands (from Whatman Inc., Fairfield, N.J.) and Nuclepore® brands (Corning Inc, Acton, Mass.)] in a variety of pore sizes (from 0.01 $\mu$m to 20 $\mu$m), in a variety of shapes (for example, 47 mm circles, 8×10 inch sheets or larger rolls) and can be made from other materials. For example, Poretics® polyester track-etch (PETE) membrane filters are precision, two dimensional, microporous screens, similar to polycarbonate track-etch (PCTE) membranes, but with better solvent resistance. One advantage of using the PETE membranes in solid-phase enzyme screening is that they are resistant to most commonly used chemicals, except for strong bases, and have been used for filtration of HPLC solvents and other chemically aggressive fluids. Track-etch membranes also offer excellent thermal stability. Polyester membranes can be repeatedly autoclaved at 121° C. (250° F.), and no damage has been observed in membranes with a sustained exposure to temperatures of 140° C. (284° F.) in air or steam. Poretics track-etch membranes range in thickness between 6–14 $\mu$m. Whatman Cyclopore track-etch membranes range in thickness from 7 to 23 $\mu$m. Many other types of membrane filters available on the market are much thicker. For example, mixed cellulose membranes from Millipore are 100–140 $\mu$m thick.

Treatment of the track-etch membrane surfaces can modify their physical characteristics significantly. This allows for tailoring the membrane to meet specific and exacting applications. For example, manufacturers have successfully modified the surface of polycarbonate membranes to make them very hydrophilic, very hydrophobic, or charged to promote selective binding of ligands or to enhance cell or microorganism attachment.

The properties of track-etch membranes make them ideal materials for imaging and analyzing microcolonies of cells. Other microporous membranes with similar properties can also be used.

The strength of track-etch membranes facilitates the transfer of microcolony-bearing membranes from one location to another. Examples of this transfer include transfer between a growth plate and induction plate or induction plate and assay plate.

Track-etch membranes permit capture of cells on a flat, smooth, almost glass-like surface with approximately uniform distribution across the membrane surface. The evenness and randomness of the distribution of pores across the surface contributes to this uniform sample deposition. The precision of the pore sizing and the narrowness of the size distribution in track-etch membranes is not achieved by other filtration media systems. Ordinary depth-type membrane filters, such as nitrocellulose, contain tortuous pores that capture particles (cells) via random entrapment. This results in the trapping of some fraction of cells in the interior (interstices) of the membrane filter.

Track-etch membranes are non-staining, a quality which provides an exceptional background for sample observations. Track-etch membranes of most pore sizes are also optically transparent or translucent. This property is useful because it facilitates illumination of the microcolony-bearing membrane from below without excessive optical absorption or scattering from the membrane itself.

Polyester track-etch membranes are resistant to the chloroform vapor used during lysis of the microcolonies on the membranes and are especially useful when evolving enzymes for activity in organic solvents. (Chemical Compatibility Table, Osmonics Poretics® Products Catalog 1997–1998 ed., p. 35; see Table 1, below). Although polycarbonate (PCTE) membranes are chemically incompatible with chloroform, microcolonies grown on polycarbonate membranes can be lysed using chloroform vapor as described in U.S. Pat. No. 5,914,245 if the membranes are wetted with aqueous buffer. The resistance of polyester track-etch membranes to chloroform allows microcolony lysis in the absence of water. Chloroform is preferred because of its high vapor pressure and its ability to rapidly lyse cells. Membranes that are chemically resistant to non-aqueous solvents are also necessary for monitoring enzymatic reactions that are performed in the presence of these solvents. In one embodiment for directed evolution of enzymatic activity in the presence of non-aqueous solvents, the desired enzymatic activity is screened in solid phase by exposing the microcolonies on a polyester membrane to a mixture of solvent and optical signal substrate. Such solvents may comprise toluene, dimethylformamide or hexane, as well as biphasic mixtures of these solvents with water. Chemical resistance of the membrane material to these non-aqueous solvents is important because it maintains the smoothness and optical homogeneity of the membrane, so that the microcolonies can be imaged with greater signal-to-noise. In addition, it provides for easier handling of the membranes without warping or curling.

TABLE 1

Chemical Compatibility of Polyester Track-Etch Membranes. Polyester track-etch membranes were exposed to the following chemicals. If there was no significant change in the bubble point, strength or appearance of the membrane, it was judged compatible with the chemical. If the membrane dissolved, or otherwise lost its strength, or changed significantly in appearance, it was rated incompatible with the liquid. A TEST rating indicates the possibility that the membrane could be useful in some operating conditions.

| Acids | | Halogenated Hydrocarbons | |
|---|---|---|---|
| Acetic, 10% | OK | Bromoform | OK |
| Acetic, Glacial | OK | Carbon Tetrachloride | OK |
| Boric, 5% | OK | Chloroform | OK |
| Formic, 50% | OK | Ethylene Dichloride | OK |
| Hydrochloric, 6N | TEST | Methylene Chloride | OK |
| Hydrochloric, conc. | NO | Tetrachloroethylene | OK |
| Hydrofluoric, 35% | OK | (perchloroethylene) | |
| Nitric, 6N | OK | 1,1,1-Trichloroethane | OK |
| Nitric, conc. | NO | 1,1,2-Trichloroethane | OK |
| Perchloric, 60% | NO | Monochlorobenzene | OK |
| Phosphoric, 85% | OK | Trichlorobenzene | OK |
| Sulfuric, 6N | OK | Trichloroethylene | OK |
| Sulfuric, conc. | NO | Hydrocarbons | |
| Alcohol's | | Benzene | OK |
| N-Amyl | OK | Cyclohexane | OK |
| Butanol | OK | Hexane | OK |
| Ethanol | OK | Pentane | OK |
| Ethylene Glycol | OK | Toluene | OK |
| Glycerol | OK | Xylene | OK |
| N-Hexanol | OK | Ketones | |
| Isobutanol | OK | Acetone | OK |
| Isopropanol | OK | Cyclohexanone | OK |
| Methanol | OK | Methyl Ethyl Ketone (MEK) | OK |
| Propanol | OK | Oils | |
| propylene Glycol | OK | Silicones | OK |
| Butyl Cellosolve | OK | Petroleum Oils | OK |
| Methyl Cellosolve | OK | Photo Resists | |
| 2,2 Ethoxyethoxy Ethanol (Carbitol) | OK | Kodak KMER and KTFR Shipley AZ-111,340,1350 | OK OK |

TABLE 1-continued

Chemical Compatibility of Polyester Track-Etch Membranes. Polyester track-etch membranes were exposed to the following chemicals. If there was no significant change in the bubble point, strength or appearance of the membrane, it was judged compatible with the chemical. If the membrane dissolved, or otherwise lost its strength, or changed significantly in appearance, it was rated incompatible with the liquid. A TEST rating indicates the possibility that the membrane could be useful in some operating conditions.

| Polyethylene Glycol | OK | Waycoat 59 | OK |
|---|---|---|---|
| Benzyl | OK | Miscellaneous | |
| Aldehydes | | Hydrogen Peroxide,30% | OK |
| Butyraldehyde | OK | Diacetone Alcohol | OK |
| Formaldehyde | OK | Nitrobenzene | OK |
| Amines | | 1-Nitropropane | OK |
| Aniline | OK | Acetonitrile | OK |
| Diethyl Acetamide | OK | Bleach, Household | OK |
| Dimethylformamide | OK | Pyridine | OK |
| Triethylamine | OK | Tetrahydrofuran | OK |
| Bases | | Dimethylsulfoxide (DMSO) | OK |
| Ammonium Hydroxide, 6N | TEST | Freon TF | OK |
| Potassium Hydroxide, 6N | NO | Mineral Spirits | OK |
| Sodium Hydroxide, 6N | NO | Turpentine | OK |
| Esters | | | |
| Amyl Acetate | OK | | |
| Butyl Acetate | OK | | |
| Ethyl Acetate | OK | | |
| Methyl Acetate | OK | | |
| Methyl Formate | OK | | |
| Ethers | | | |
| 1,4 Dioxane | OK | | |
| Ethyl Ether | OK | | |
| Isopropyl Ether | OK | | |
| Petroleum Ether | OK | | |
| Fuels | | | |
| Gasoline | OK | | |
| Jet Fuel 640A | OK | | |
| Kerosene | OK | | |

OK = Recommended
NO = Not Recommended
TEST = Testing Advised

Due to the unique pore structure of PCTE and PETE track-etch membranes, they exhibit lower holdup volumes than many other filter materials. For example, Poretics PCTE membranes exhibit extremely low absorption and adsorption losses, varying from 3 to 6% of the membrane volume. Absorption refers to entrapment of the substrate solution within the structure of the membrane. Adsorption refers to reversible surface interactions (e.g., ionic, van der Waals, or hydrogen bonding interactions) between the molecules of the substrate solution and the membrane material. In comparison to the track-etch membranes, tortuous cellulosic filters adsorb from 40 to 64%, depending on the molecule. This negligble adsorption of solution significantly contributes to the low effective assay volumes possible in our high throughput solid phase screening system. Fluid absorption, measured by immersing the track-etch membrane samples in water for 24 hours, causes an average membrane weight gain of only 0.24%. The usefulness of a given membrane material for solid-phase screening can therefore be determined by weighing the filter before and after wetting it with a minimal amount of substrate solution and determining the increase in mass of the wet filter due to absorption and adsorption of the solution. Membrane materials with the lowest wet/dry mass ratios are preferred because they require less substrate per assay.

The reduced thickness of track-etch membranes relative to other filter membranes allows more rapid diffusion across the membrane when contacting the membrane containing microcolonies with an optical signal substrate from the opposite side of the membrane. This reduces the lag in initiating the desired chemical reaction that can be observed when using thicker filter membranes. The resulting kinetic data obtained using these thinner assay membrane filters results in the acquisition of higher quality kinetic data.

The invention described in U.S. Pat. No. 5,914,245 provides a method of performing solid-phase directed evolution enzyme screening and includes a concise presentation of a preferred embodiment of this method. This 11-step method begins with the gene encoding an enzyme and concludes with the isolation of an "evolved" enzyme with improved properties under selection.

1. Error-prone PCR is used to randomly mutagenize the enzyme-encoding DNA. The DNA is transformed into *E. coli* to make a library of mutants expressing enzyme variants.
2. The library is deposited on 47 mm diameter assay disks to generate a density of 200–500 colonies/cm$^2$ and the cells on the disks are grown on agar plates until microcolonies (about 100 µm diameter) appear.
3. The assay disk (with colony side up) is transferred to an induction plate containing IPTG and grown at 30 degree C. for 4–5 hours (about 200 µm diameter).
4. The assay disk is transferred to a "lysis chamber" where it is covered with a thin film of aqueous buffer and exposed briefly to chloroform vapor.
5. The MicroColonyImager is prepared for a kinetics run by setting software and hardware parameters so that they are suitable for a given calorimetric indicator. The instrument is set to 615 nm in absorption mode for X-gal (5-Bromo-4-chloro-3-indolyl-beta-galactoside). Hydrolysis of the X-gal by a glucosidase generates an indoxyl intermediate, which spontaneously dimerizes to form blue indigo.
6. The assay disk bearing microcolonies is transferred to the MicroColonyImager sample/reaction compartment, which contains a paper wick. The wick ensures that the membrane is uniformly bathed in a chromogenic substrate at saturating concentrations. Approximately 0.5–1 ml of substrate is added (at 1 mg/ml for galactosides or glucosides).
7. The disk is imaged at set time intervals for approximately one hour (or until the microcolony color is fully developed to the endpoint).
8. The MicroColonyImager highlights microcolonies that display the highest absorbance, while insuring that the change in absorbance with respect to time is linear, indicative of an initial enzyme velocity. In multiple substrate experiments, spectroscopic data are acquired for the different chromogenic substrates.
9. The desired portion of the assay disk (at the position of a "positive" microcolony) is recovered by hand with Pasteur pipettes. The disk portion is transferred to a tube containing a buffered solution and the DNA obtained is re-transformed.
10. Positive colonies are separately grown and analyzed in vitro, so that the essential enzymatic parameters such as $K_m$, $k_{cat}$, substrate specificity, and enantiomeric excess (ee) can be determined.
11. Based on measured improvement in such factors, one variant is picked, and steps 1–10 are repeated for each cycle of directed evolution in the random sequential mutagenesis method until a mutant enzyme with the desired characteristics is obtained.

This 11-step method can be modified in many ways using other procedures. The following examples of these modifications are intended to illustrate but not limit the invention. While they are typical of those that might be used, other procedures known to those skilled in the art may alternatively be used. While this method is described for an absorption mode and chromogenic substrates, the method can also use enzyme model systems using fluorogenic and FRET substrates.

U.S. Pat. No. 5,914,245 describes the assay disk used as ranging in size from 47 mm to 82 mm. For example, in the 11-step method described above, a bacterial library is deposited on 47 mm diameter assay disks to generate a density of 200–500 colonies/cm$^2$ and, the cells on the disks are then placed in contact with growth medium until microcolonies (about 100 microns in diameter) appear. By increasing the diameter of the disk from 47 to 82 mm, and roughly doubling the density of the colonies, about 50,000 microcolonies per disk can be analyzed. Alternatively, the number of microcolonies that can be analyzed in the MicroColony-Imager can be increased further by depositing a bacterial library upon assay membranes of larger sizes or different shapes. For example, microcolonies can be grown on rectangular track-etch membranes, such as PETE, placed in contact with growth medium in 86×128 mm Nalge Nunc (242811) OmniPlates or similar single-well microtiter plates.

A number of procedures can be used for applying an inoculum to the assay filter membranes. The membrane provides a substantially continuous base for imaging and analyzing microcolonies of cells. In one embodiment, cells are deposited onto 47 mm-diameter membranes by vacuum filtration. For example, the nitrocellulose filter provided in a Nalgene 130-4020 Analytical Filter unit can be replaced with a 47 mm-diameter track-etch membrane filter. A solution containing the cells to be deposited is poured into the modified filter unit, and a vacuum is applied to draw the solution through the membrane, leaving the cells deposited on the membrane surface. Alternatively, cells can be deposited on larger format filters by using a large-format vacuum manifold employing fritted glass or plastic or a fine mesh as the filter support. If bacteria are being deposited, the membrane can be transferred to a dish containing nutrient agar, and the cells can be incubated until microcolonies form. In another procedure, cells can be spread over an assay filter membrane by aerosolization, using an aerosol deposition device, such as an airbrush or a manually pumped sprayer within a biologically contained laminar flow hood. In a simple and effective method, cells are deposited on the assay filter membrane using fine glass beads, approximately 1–3 mm in diameter. This can be done after a polymer filter membrane has already been placed in contact with the nutrient agar or other appropriate media in a Petri dish, OmniPlate, or larger-format Petri tray. For this method, fine glass beads are added to a solution containing cells, and this bacteria/glass bead slurry is spread evenly over the surface with a spreader made of glass, plastic or metal. Alternatively, glass beads and a solution containing cells are separately poured onto the assay filter membrane and the dish or tray containing the membrane is shaken to spread the solution across the filter with the beads. When the cells have been spread across the membrane and the filter has partially dried, the beads can be removed. The polymer filter on the agar can then placed in an incubator, if necessary, to allow microcolonies to form.

During the fourth step in the 11-step method, the assay membrane filter can be transferred to a "lysis chamber"

where it is exposed briefly to chloroform vapor. In an alternative method, the assay membrane filter is exposed to chloroform vapor while it is still in contact with the nutrient agar or induction plate. For example, 47 mm assay filter membranes can be exposed to chloroform vapor as follows: A Nalgene 130-4020 Analytical Filter unit is disassembled and its porous cardboard wafer is placed into the top half of the plastic filter unit. This top half of the filtration apparatus is placed directly over the membrane containing the microcolonies while the assay filter membrane is still on induction plate. The cardboard wafer in the filtration apparatus is one or two centimeters above the membrane. Once the upper filtration unit is positioned over the membrane, about 1 ml of chloroform is added to the wafer in an appropriate chemical hood, using a smooth outwardly spiraling motion. The apparatus is then covered with a plastic lid and allowed to stand for 45–60 seconds. The filtration unit is removed from the plate, and the induction plate containing the membrane with lysed colonies is immediately transferred to the MCI device to start a measurement. In another example, filter paper (e.g. Scleichter & Schuell Gel Blot paper) is attached to the inside of a plastic lid from a nutrient agar or induction plate. Chloroform is then added to this piece of filter paper and the lid is placed back onto the plate or dish, suspending the chloroform-soaked filter paper over the filter membrane that contains the microcolonies. The microcolony-covered assay filter membrane is exposed to the chloroform vapor for about 60 seconds. The assay filter membrane bearing microcolonies is then transferred to the MicroColonyImager sample/reaction compartment.

For assaying enzyme activity, the filter containing the microcolonies is transferred onto a wick that is saturated with an optical signal substrate or substrates. Contact between the membrane containing the microcolonies and the wick is used for synchronously initiating a chemical reaction in the microcolonies that express active enzyme. The wick containing optical signal substrate may comprise any of a number of different materials. In U.S. Pat. No. 5,914,245, a paper wick was used in the described examples. In one embodiment, the wick comprises a freely diffusible reactant. The freely diffusible reactants may comprise optical signal substrates that are appropriate for the enzyme activity being assayed. These may include enzyme substrates, indicators, indicator enzymes, inhibitors, and the like. In a new embodiment, the wick comprises a gel of buffered 1% agarose that is homogeneously mixed with optical signal substrate. The agarose wick can formed by heating the agarose in a buffer solution in the microwave until the agarose is thoroughly dissolved. After the agarose solution has partially cooled, the optical signal substrate material is added and thoroughly mixed. A thin layer of the agarose (approximately 2–3 mm thick) is then poured into a suitable mold, such as a plastic petri dish, and allowed to solidify to create a wick. The use of an agarose wick is advantageous for solid-phase screening of enzymes in microcolonies because it provides improved uniformity for the enzyme reaction. Alternatively, the gel may comprise about 5–20% polyacrylamide. Methods for creating polyacrylamide gels are well known in the art (see, e.g., Sambrook et al., 1989).

There are a number of additional polymers that can be used to create gels that are useful as wicks. For example, a 12% starch gel can be made by placing a 2× slurry of starch that is uniformly suspended in buffer into a vacuum flask. An equal volume of buffer solution heated to boiling is then quickly mixed with this slurry. The 1× slurry is then further heated briefly in a microwave to completely dissolve the starch. After cooking, the starch slurry is degassed by applying a vacuum to the flask. After the slurry has partially cooled, the optical signal substrate materials are added and thoroughly mixed. The wick can then be formed as described above for the agarose example. Other polymeric materials may be fashioned into gel-based wicks in a similar manner. In some cases, it may also be preferable to mix a given polymer with agarose. These polymers include cellulose, xylan, guar, chitin, locust bean gum, and pectin.

In another embodiment, the wick comprises a non-freely diffusible reactant. Thus, for example, the wick material can itself be a substrate for the enzyme whose activity is being measured, as described in the section on assays (vide supra). In this embodiment, the wick may comprise a polymer gel or a viscous solution of a polymeric material such as starch or cellulose that is used to assay amylase or cellulase activity in microcolonies. The wick may also comprise a dye, such that enzymatic activity in the microcolonies changes the optical properties of the dye. Thus, for example, starch heavily labeled with BODIPY FL (obtained from Molecular Probes; Eugene, Oreg.) can be incorporated into the wick material. The fluorescence of the dye is quenched until its constituent oligosaccharides are released by the action of amylase. Amylase activity expressed in microcolonies can therefore be assayed by exciting the sample at about 503 nm and detecting the increase fluorescence emission over time at about 512 nm. Other polymers can be incorporated into a wick as non-freely diffusible reactants. Examples of these polymers include agarose, cellulose, xylan, guar, chitin, locust bean gum and pectin.

A Compact and Temperature-Controlled MCI Device

The MicroColonyImager (MCI) embodied in FIG. 1 of U.S. Pat. No. 5,914,245 uses an integrating sphere to achieve even illumination of the assay disk. Advantages of the integrating sphere over other means of illuminating the sample include uniformity of lighting, and the ability to image the sample at either the baffle or the exit port such that both opaque and transparent targets, respectively, can be illuminated. For some applications, particularly those involving translucent samples, we have modified the MCI according to FIG. 1 of the present invention so as to replace the bulky integrating sphere with a folded optical pathway comprising two mirrors and two light diffusers. This configuration is also more amenable to temperature control, because the sample compartment is smaller than that required within an integrating sphere.

FIG. 1 shows the improved compact, temperature-controlled MCI unit. The modified device comprises a diffuser interposed between the light source and the target for dispersing the emitted light to uniformly illuminate the target in the sample compartment, a folded light path between the light source and the camera, and a temperature-controlled forced-air heating system for maintaining the temperature of the microcolonies of cells on the target. As in the device exemplified in U.S. Pat. No. 5,914,245, the light path begins at a computer-interfaced light source and monochromator (1), then travels through a liquid light guide (2) to a projection device (3) which holds a lens (4) and a holographic light diffuser (5). The light source and light-filtering device can alternatively be a filter wheel (such as model Lambda 10-2 from Sutter Instrument Company, Novato, Calif.) or other devices known to produce monochromatic light. The light guide (2) can be a 5 mm diameter light guide from Edmund Industrial Optics (Barrington, N.J.), model H53691. Alternatively, this may be a glass, quartz, or silica fiber optic. The lens (4) is a 33 mm fl 25 mm diameter UV-grade fused silica lens with a broad-band anti-reflective coating. The focal length and size of the lens can be varied to fit alternative packaging of the optical components for longer or shorter pathlengths. The holographic light diffuser (5) can be a 15 degree diffusing angle device as supplied by Oriel (Stratford, Conn.) in 25 mm diameter as model J54-494. Light is projected onto and reflected by a mirror (6) so as to save space within the instrument. Light enters the temperature-controlled sample compartment (7) through an optical glass diffuser (8) such that the assay disk (9) is evenly illuminated without significant light loss. The optical glass diffuser can be a 6 inch diameter flashed opal diffuser from Oriel, model number 48060. The assay disk is imaged through the transparent top of the sample compartment (7) through a rectangular anti-reflective glass window (26). Surfaces 25 and 26 are labeled on shaded corners of these two surfaces of the sample compartment merely to indicate perspective in the drawing. The glass window (26) can be a 5-inch×7-inch large format coated window, model number H43973 from Edmund Industrial Optics (Barrington, N.J.). The imaging pathway is folded to conserve space within the instrument by using a mirror (10) placed at a 45 degree angle with respect to the objective lens (11) of a CCD camera (12). The camera is controlled and delivers image data through a cable (13) to a computer (14). The computer also controls the monochromator wavelength through cable (15). As previously described in U.S. Pat. No. 5,914,245, filters can be placed at a position in front of the objective lens (11) so as to facilitate fluorescence imaging. The folded, compact design described here is consistent with the use of a filter wheel directly in front of the objective lens.

Airflow through the sample compartment achieves uniform temperature control of the assay disk (9) by a temperature feedback circuit and electrical heater. Sensor (16) is attached to a thermally insulated post (17) such that it can measure the air temperature within the chamber. The sensor sends an electrical signal through a cable (18) to a controller (19), which increases the power through cable (20) applied to warming the intake air (21) by the heating element (22). The heating element is a Master Appliance (Racine, Wis.) model 20012 260 degree C. element from a Master-Mite type heat gun, model 10008. This heating element is connected using a component from Master appliance which has a temperature cut-out. While the unit is in operation, the sample compartment is relatively air tight, and so a vent (23) is provided for exhausted air (24). Forced air is provided by fans and a system of plenums connected to the heater (not shown). A system of rails and assay disk holder have been constructed such that the assay disk (9) remains attached to the front surface (25) of the sample compartment (7) when it is opened. This provides overhead access to the assay disk when the door is pulled forward.

The heat controller (19) includes an electronic servo system that regulates the duty cycle of the heating element in order to maintain the required temperature between ambient and about 80 degrees C. The temperature servo system consists of various analog circuits on a printed wiring board, a digital potentiometer, and an RTD, or resistance temperature detector (16), which acts as the temperature sensor. The RTD is mounted in the stream of air flowing out of the heater element. The temperature set point is entered on the digital potentiometer, and an analog proportional-integral-derivative (PID) circuit adjusts the duty cycle of the heater element so that the temperature indicated by the RTD matches the temperature set point. The blower, heating element, and exhaust port were selected to obtain a rate of air exchange sufficient for good temperature control given the sample compartment size.

The camera (12) can be a monochrome CCD camera or an RGB CCD camera, such as a Quantix model 6301 from Roper Scientific (Tucson, Ariz.) or a Sony XC-003 3-CCD color video camera vended through Edmund Industrial Optics. In the case of the monochrome camera, a 5 MHz download rate enables the camera to transfer a. 6 megapixel image in approximately 1.2 seconds. In combination with a computer interfaced monochromator (1) such as a model SID-201 from Photon Technology International, Inc. (Monmouth Junction, N.J.), the time interval within which an image can be recorded and then changed to a second wavelength is on the order of 2 seconds. Thus, an RGB image can be acquired by changing the position of the monochromator grating in concert with recording images within a period of about six seconds. This time difference is very small compared to the cycle time of forming a kinetics image stack, in which images are acquired approximately every 2 minutes. An alternative means for generating a series of RGB images is to use the Sony XC-003 3-CCD color video camera, which produces RGB images at a video rate. In the case of a color video camera, the light source is a white light source, and does not require a monochromator. The advantage of using a monochrome camera with a monochromator or filter wheel is that the spectral aspect of the temporal series of images can be increased above three-channel RGB data to 4 or more channels. These channels can be at wavelengths of particular interest as opposed to the RGB camera, which may be set according to the constraints of certain built-in broadband RGB filters. In either embodiment, a temporal series of multichannel (e.g., multiwavelength) images are obtained for further processing. This description of cameras is not meant to be limited to CCD detectors in that other devices could be used to record multiple wavelength images as a function of time and record a pixel image with respect to time. Advances in digitization and download times as well as increases in CPU cycle time and connectivity (e.g., ethernet, firewire, and the like) are expected to reduce the cycle time for acquiring this multichannel data.

REFERENCES CITED

Akkara, J. A., Ayyagari, M. S. & Bruno, F. F. (1999) *Trends. Biotechnol.* 17:67–73.
Arkin, A. P. & Youvan, D. C. (1992) *Proc. Natl. Acad. Sci. U.S.A.* 89:7811–7815.
Bornscheuer, U. T., Altenbuchner, J. & Meyer, H. H. (1999) *Biorg. Med. Chem.* 7:2169–2173.
Bull, A. T., Bunch, A. W. & Robinson, G. K. (1999) *Curr. Opin. Microbiol.* 2:246–251.
Chen, K. & Arnold. F. H. (1991) *Biotechnology (N.Y.)* 9:1073–1077.
Chen, K. & Arnold. F. H. (1993) *Proc. Natl. Acad. Sci. U.S.A.* 90:5618–5622.
Crane, R. K. & Sols, A. (1960) *Methods Enzymol.* 1:277.
Cristol, P., Nicolas, J. C., Chabab, A. & Diafouka, F. (1985) *Ann. Biol. Clin.* (Paris) 43:878–884.
Dahiyat, B. I. & Mayo, S. L. (1996) *Protein Sci.* 5:895–903.
Dahiyat, B. I., Sarisky, C. A. & Mayo, S. L. (1997) *J. Mol. Biol.* 273: 789–796.
Dahiyat, B. I. (1999) *Curr. Opin. Biotechnol.* 10:387–390.
Darrow, R. A. & Colowick, S. P. (1962) In *Methods in Enzymology, Vol. V.,* (Colowick, S., & Kaplan, N., eds.), Academic Press, New York, 226 (1962).
Delagrave, S. & Youvan, D. C. (1993) Biotechnology (N.Y.) 11:1548–1552.
Delagrave, S., Goldman, E. R. & Youvan, D. C. (1993) *Protein Eng.* 6:327–331.

Dona, V. (1985) *J. Immunol. Methods* 82:65–75.
Hutchinson, C. R. (1998) *Curr. Opin. Microbiol.* 1:319–329.
Jacobsen, J. R. & Khosla, C. (1998) *Curr. Opin. Chem. Biol.* 2:133–137.
Jaeger, K. E., Adrian, F. J., Meyer, H. E., Hancock, R. E. & Winkler, U. K. (1992) *Biochim. Biophys. Acta* 1120:315–321.
Joo, H., Arisawa, A., Lin, Z. & Arnold, F. H. (1999) *Chemistry and Biology* 6:699–706.
Khalifah, R. G. (1971) *J. Biol. Chem.* 246:2561–2573.
Lowry, O. H., Roberts, N. R., Wu, M.-L., Hixon, W. S. & Crawford, E. J. (1951) *J. Biol. Chem.* 207:19–37.
Marrs, B., Delagrave, S. & Murphy, D. (1999) *Curr. Opin. Microbiol.* 2:241–245.
Moore, J. C. & Arnold, F. H. (1996) *Nat Biotechnol.* 14:458–467.
Moris-Varas, F., Shah, A., Aikens, J., Nadkarni, N. P., Rozell, J. D. & Demerjian, D. C. (1999) *Bioorg. Med. Chem.* 7:2183–2188.
Nachlas, M., Marquilies, S., Goldberg, J. & Seligman, A. (1960) *Anal. Biochem.* 1: 317.
Nielsen, J. (1998) *Biotechnol. Bioeng.* 58:125–132.
Ogawa, J. & Shimizu, S. (1999) *Trends Biotechnol.* 17:13–21.
Rosenberg, R. M., Herreid, R. M., Piazza, G. J. & O'Leary, M. H. (1989) *Anal. Biochem.* 181:59–65.
Sambrook, J., Fritsch, E. F. & Maniatis, T. (1989) *Molecular Cloning: A Laboratory Manual*, $2^{nd}$ ed., Cold Spring Harbor Laboratory Press, Plainview, N.Y.
Singer, B. & Kusmierek, J. T. (1982) *Annu. Rev. Biochem.* 51:655–693.
Stemmer, W. P. (1994a) *Nature* 370:389–391.
Stemmer, W. P. (1994b) *Proc. Natl. Acad. Sci. U.S.A.* 91:10747–10751.
Takahashi, A., Camacho, P., Lechleiter, J. D. & Herman, B. (1999) *Physiol. Rev.* 79:1089–1125.
Uhlig, H. (1998) *Industrial Enzymes and Their Applications*, John Wiley & Sons, New York.
Wajzer, J. (1949) *Hebd. Seances Acad. Sci.* 229:1270.
Whittaker, R. G., Manthey, M. K., LeBrocque, D. S. & Hayes, P. J. (1994) 220:238–243.

All publications, patent applications, patents, and other references mentioned herein are incorporated by reference in their entirety. In the case of conflict, the present application, including definitions, will control. In addition, the materials, methods, and examples described herein are non-limiting illustrations only and the invention is to be limited only by the scope of the appended claims.

What is claimed:

1. A method for imaging and analyzing microcolonies of cells, including the steps of:
    forming in excess of 100 regions, each region including at least one biological cell on a substantially continuous base at an average density of at least about 10 regions per square centimeter, the base comprising a microporous membrane;
    initiating a chemical reaction in such regions that results in an optically detectable signal that changes over time;
    automatically optically monitoring each region over time for changes in the optical signal of portions of such regions; and
    indicating which of such portions have a desired change in optical signal.

2. The method of claim 1, wherein the microporous membrane is a track-etch membrane.

3. The method of claim 2, wherein the track-etch membrane is a polyester track-etch membrane.

4. The method of claim 2, wherein the track-etch membrane is a polycarbonate track-etch membrane.

5. The method of claim 1, wherein the microporous membrane thickness is less than or equal to about 20 micrometers.

6. The method of claim 1, wherein the path of the pores through the microporous membrane is non-tortuous.

7. The method of claim 1, wherein the microporous membrane is chemically resistant to non-aqueous solvents.

8. The method of claim 7, wherein the non-aqueous solvent comprises chloroform.

9. The method of claim 7, wherein the non-aqueous solvent comprises toluene.

10. The method of claim 7, wherein the non-aqueous solvent comprises dimethylformamide.

11. The method of claim 7, wherein the non-aqueous solvent comprises hexane.

12. The method of claim 1, wherein the microporous membrane is optically transparent.

13. The method of claim 1, wherein the microporous membrane is optically translucent.

14. The method of claim 1, wherein the mass of the microporous membrane is less than 100 times the mass of substrate solution absorbed or adsorbed by the membrane.

15. The method of claim 1, wherein the mass of the microporous membrane is less than 10 times the mass of substrate solution absorbed or adsorbed by the membrane.

16. The method of claim 1, wherein the mass of the microporous membrane is less than or equal to the mass of substrate solution absorbed or adsorbed by the membrane.

17. A method of performing solid-phase directed evolution enzyme screening, including the steps of:
    generating an average density of at least 10 microcolonies of cells per square centimeter on a solid phase, the solid phase comprising a microporous membrane, and wherein a plurality of microcolonies express variants of at least one enzyme;
    contacting the expressed variants with at least one optical signal substrate, each indicative of a desired enzymatic activity; and
    automatically detecting changes over time in one or more optical signals generated by one or more optical signal substrates in the microcolonies, wherein such changes indicate desired enzymatic activity of the variants of the enzyme.

18. The method of claim 17, wherein the microporous membrane is a track-etch membrane.

19. The method of claim 18, wherein the track-etch membrane is a polyester track-etch membrane.

20. The method of claim 18, wherein the track-etch membrane is a polycarbonate track-etch membrane.

21. The method of claim 17, wherein the microporous membrane thickness is less than or equal to about 20 micrometers.

22. The method of claim 17, wherein the path of the pores through the microporous membrane is non-tortuous.

23. The method of claim 17, wherein the microporous membrane is chemically resistant to non-aqueous solvents.

24. The method of claim 23, wherein the non-aqueous solvent comprises chloroform.

25. The method of claim 23, wherein the non-aqueous solvent comprises toluene.

26. The method of claim 23, wherein the non-aqueous solvent comprises dimethylformamide.

27. The method of claim 23, wherein the non-aqueous solvent comprises hexane.

28. The method of claim 17, wherein the microporous membrane is optically transparent.

29. The method of claim 17, wherein the microporous membrane is optically translucent.

30. The method of claim 17, wherein the mass of the microporous membrane is less than 100 times the mass of substrate solution absorbed or adsorbed by the membrane.

31. The method of claim 17, wherein the mass of the microporous membrane is less than 10 times the mass of substrate solution absorbed or adsorbed by the membrane.

32. The method of claim 17, wherein the mass of the microporous membrane is less than or equal to the mass of substrate solution absorbed or adsorbed by the membrane.

33. A method of performing solid-phase enzyme discovery screening, including the steps of:
generating a density of at least 10 microcolonies of cells per square centimeter on a solid phase, the solid phase comprising a microporous membrane, and wherein a plurality of microcolonies consist of cells containing members of a recombinant DNA library;
contacting the microcolonies with at least one optical signal substrate, each indicative of a desired enzymatic activity; and
automatically detecting changes over time in one or more optical signals generated by one or more optical signal substrates in the microcolonies, wherein such changes indicate desired enzymatic activity.

34. The method of claim 33, wherein the microporous membrane is a track-etch membrane.

35. The method of claim 34, wherein the track-etch membrane is a polyester track-etch membrane.

36. The method of claim 34, wherein the track-etch membrane is a polycarbonate track-etch membrane.

37. The method of claim 33, wherein the microporous membrane thickness is less than or equal to about 20 micrometers.

38. The method of claim 33, wherein the path of the pores through the microporous membrane is non-tortuous.

39. The method of claim 33, wherein the microporous membrane is chemically resistant to non-aqueous solvents.

40. The method of claim 39, wherein the non-aqueous solvent comprises chloroform.

41. The method of claim 39, wherein the non-aqueous solvent comprises toluene.

42. The method of claim 39, wherein the non-aqueous solvent comprises dimethylformamide.

43. The method of claim 39, wherein the non-aqueous solvent comprises hexane.

44. The method of claim 33, wherein the microporous membrane is optically transparent.

45. The method of claim 33, wherein the microporous membrane is optically translucent.

46. The method of claim 33, wherein the mass of the microporous membrane is less than 100 times the mass of substrate solution absorbed or adsorbed by the membrane.

47. The method of claim 33, wherein the mass of the microporous membrane is less than 10 times the mass of substrate solution absorbed or adsorbed by the membrane.

48. The method of claim 33, wherein the mass of the microporous membrane is less than or equal to the mass of substrate solution absorbed or adsorbed by the membrane.

49. A method of performing solid phase directed evolution enzyme screening, wherein the solid phase comprises a track-etch membrane.

50. The method of claim 49, wherein the track-etch membrane is a polyester track-etch membrane.

51. The method of claim 49, wherein the track-etch membrane is a polycarbonate track-etch membrane.

52. A method of performing solid phase directed evolution enzyme screening, wherein the solid phase comprises a microporous membrane whose thickness is less than or equal to about 20 micrometers.

53. A method of performing solid phase directed evolution enzyme screening, wherein the solid phase comprises a microporous membrane wherein the path of the pores through the microporous membrane is non-tortuous.

54. A method of performing solid phase directed evolution enzyme screening, wherein the solid phase comprises a microporous membrane which is optically transparent.

55. A method of performing solid phase directed evolution enzyme screening, wherein the solid phase comprises a microporous membrane which is optically translucent.

56. A method of performing solid phase directed evolution enzyme screening, wherein the solid phase comprises a microporous membrane, and wherein the mass of the microporous membrane is less than 100 times the mass of substrate solution absorbed or adsorbed by the membrane.

57. A method of performing solid phase directed evolution enzyme screening, wherein the solid phase comprises a microporous membrane, and wherein the mass of the microporous membrane is less than 10 times the mass of substrate solution absorbed or adsorbed by the membrane.

58. A method of performing solid phase directed evolution enzyme screening, wherein the solid phase comprises a microporous membrane, and wherein the mass of the microporous membrane is less than or equal to the mass of substrate solution absorbed or adsorbed by the membrane.

59. A method of performing solid-phase enzyme discovery screening, wherein the solid phase comprises a track-etch membrane.

60. A method of claim 59, wherein the track-etch membrane is a polyester track-etch membrane.

61. The method of claim 59, wherein the track-etch membrane is a polycarbonate track-etch membrane.

62. A method of performing solid-phase enzyme discovery screening, wherein the solid phase comprises a microporous membrane whose thickness is less than or equal to about 20 micrometers.

63. A method of performing solid-phase enzyme discovery screening, wherein the solid phase comprises a microporous membrane in which the path of the pores through the microporous membrane is non-tortuous.

64. A method of performing solid-phase enzyme discovery screening, wherein the solid phase comprises a microporous membrane which is optically transparent.

65. A method of performing solid-phase enzyme discovery screening, wherein the solid phase comprises a microporous membrane which is optically translucent.

66. A method of performing solid-phase enzyme discovery screening, wherein the solid phase comprises a microporous membrane where the mass of the microporous membrane is less than 100 times the mass of substrate solution absorbed or adsorbed by the membrane.

67. A method of performing solid-phase enzyme discovery screening, wherein the solid phase comprises a microporous membrane where the mass of the microporous membrane is less than 10 times the mass of substrate solution absorbed or adsorbed by the membrane.

68. A method of performing solid-phase enzyme discovery screening, wherein the solid phase comprises a microporous membrane where the mass of the microporous membrane is less than or equal to the mass of substrate solution absorbed or adsorbed by the membrane.

69. A method for imaging and analyzing microcolonies of cells, including the steps of:
forming in excess of 100 regions, each region including at least one biological cell on a substantially continuous base at an average density of at least about 10 regions per square centimeter;

initiating a chemical reaction in such regions that generates a reaction product and results in an optically detectable signal that changes over time, wherein the signal arises from an interaction between the reaction product and an indicator;

automatically optically monitoring each region over time for changes in the optical signal of portions of such regions; and indicating which of such portions have a desired change in optical signal.

70. The method of claim 69, wherein the chemical reaction comprises the use of a hydrolase.

71. The method of claim 70, wherein the hydrolase is an esterase.

72. The method of claim 70, wherein the hydrolase is a lipase.

73. The method of claim 70, wherein the hydrolase is an amidase.

74. The method of claim 70, wherein the hydrolase is a hydantoinase.

75. The method of claim 70, wherein the hydrolase is a protease.

76. The method of claim 69, wherein the indicator is a pH indicator.

77. The method of claim 69, wherein the indicator is a redox indicator.

78. The method of claim 69, further comprising the use of an inhibitor of the chemical reaction.

79. The method of claim 78, wherein the inhibitor is an enzyme inhibitor.

80. The method of claim 79, wherein the inhibitor is a herbicide.

81. The method of claim 69, wherein the signal arises by a direct interaction between the reaction product and the indicator.

82. The method of claim 81, wherein the indicator is a pH indicator.

83. The method of claim 81, wherein the indicator is a redox indicator.

84. The method of claim 69, wherein the signal arises by an indirect interaction between the reaction product and the indicator.

85. The method of claim 84, wherein the indirect interaction is mediated by at least one indicator enzyme.

86. The method of claim 85, wherein the reaction product is hydrogen peroxide.

87. The method of claim 85 wherein the indicator enzyme is a peroxidase.

88. The method of claim 87, wherein the peroxidase is selected from the group consisting of horseradish peroxidase, soybean peroxidase, haloperoxidase, myeloperoxidase, cytochrome c peroxidase, tulip peroxidase, lignin peroxidase, carrot peroxidase, peanut peroxidase, and peroxidase Novozyme® 502.

89. The method of claim 87, wherein the peroxidase is horseradish peroxidase.

90. The method of claim 87, wherein the peroxidase is soybean peroxidase.

91. The method of claim 85, wherein the reaction product is not a substrate for the indicator enzyme.

92. A method of performing solid-phase directed evolution enzyme screening, including the steps of:

generating an average density of at least 10 microcolonies of cells per square centimeter on a solid phase, wherein a plurality of microcolonies express variants of at least one enzyme;

contacting the expressed variants with at least one optical signal substrate, each indicative of a desired enzymatic activity; wherein the optical signal substrate interacts directly with the enzyme being screened, and automatically detecting changes over time in one or more optical signals generated by one or more optical signal substrates in the microcolonies, wherein such changes indicate desired enzymatic activity of the variants of the enzyme.

93. A method of performing solid-phase directed evolution enzyme screening, including the steps of:

generating an average density of at least 10 microcolonies of cells per square centimeter on a solid phase, wherein a plurality of microcolonies express variants of at least one enzyme;

contacting the expressed variants with at least one optical signal substrate, each indicative of a desired enzymatic activity; and automatically detecting changes over time in one or more optical signals generated by one or more optical signal substrates in the microcolonies, wherein the signal arises from an interaction between a product of the enzymatic activity and the optical signal substrate, and wherein such changes indicate desired enzymatic activity of the variants of the enzyme.

94. The method of claim 93, wherein the desired enzymatic activity comprises a hydrolase activity.

95. The method of claim 94, wherein the hydrolase activity is an esterase activity.

96. The method of claim 94, wherein the hydrolase activity is a lipase activity.

97. The method of claim 94, wherein the hydrolase activity is an amidase activity.

98. The method of claim 94, wherein the hydrolase activity is a hydantoinase activity.

99. The method of claim 94, wherein the hydrolase activity is a protease activity.

100. The method of claim 93, wherein the optical signal substrate is a pH indicator.

101. The method of claim 93, wherein the optical signal substrate is a redox indicator.

102. The method of claim 93, further comprising the use of an enzyme inhibitor.

103. The method of claim 102, wherein the inhibitor is a herbicide.

104. The method of claim 93, wherein the signal arises by a direct interaction between a product of the enzymatic activity and the optical signal substrate.

105. The method of claim 104, wherein the optical signal substrate is a pH indicator.

106. The method of claim 104, wherein the optical signal substrate is a redox indicator.

107. The method of claim 93, wherein the signal arises by an indirect interaction between a product of the enzymatic activity and the optical signal substrate.

108. The method of claim 107, wherein the indirect interaction is mediated by at least one indicator enzyme.

109. The method of claim 108, wherein the product of the enzymatic activity is hydrogen peroxide.

110. The method of claim 108 wherein the indicator enzyme is a peroxidase.

111. The method of claim 110, wherein the peroxidase is selected from the group consisting of horseradish peroxidase, soybean peroxidase, myeloperoxidase, cytochrome c peroxidase, tulip peroxidase, lignin peroxidase, carrot peroxidase, peanut peroxidase, and peroxidase Novozyme® 502.

112. The method of claim 110, wherein the peroxidase is horseradish peroxidase.

113. The method of claim 110, wherein the peroxidase is soybean peroxidase.

114. The method of claim 108, wherein the reaction product is not a substrate for the indicator enzyme.

115. A method of performing solid-phase enzyme discovery screening, including the steps of:
generating a density of at least 10 microcolonies of cells per square centimeter on a solid phase, wherein a plurality of microcolonies consist of cells containing members of a recombinant DNA library;
contacting the microcolonies with at least one optical signal substrate, each indicative of a desired enzymatic activity; and
automatically detecting changes over time in one or more optical signals generated by one or more optical signal substrates in the microcolonies, wherein the signal arises from an interaction between a product of the enzymatic activity and the optical signal substrate, and wherein such changes indicate desired enzymatic activity.

116. The method of claim 115, wherein the desired enzymatic activity comprises a hydrolase activity.

117. The method of claim 116, wherein the hydrolase activity is an esterase activity.

118. The method of claim 116, wherein the hydrolase activity is a lipase activity.

119. The method of claim 116, wherein the hydrolase activity is an amidase activity.

120. The method of claim 116, wherein the hydrolase activity is a hydantoinase activity.

121. The method of claim 116, wherein the hydrolase activity is a protease activity.

122. The method of claim 115, wherein the optical signal substrate is a pH indicator.

123. The method of claim 115, wherein the optical signal substrate is a redox indicator.

124. The method of claim 115, further comprising the use of an enzyme inhibitor.

125. The method of claim 124, wherein the inhibitor is a herbicide.

126. The method of claim 115, wherein the signal arises by a direct interaction between a product of the enzymatic activity and the optical signal substrate.

127. The method of claim 126, wherein the optical signal substrate is a pH indicator.

128. The method of claim 126, wherein the optical signal substrate is a redox indicator.

129. The method of claim 115, wherein the signal arises by an indirect interaction between a product of the enzymatic activity and the optical signal substrate.

130. The method of claim 129, wherein the indirect interaction is mediated by at least one indicator enzyme.

131. The method of claim 130, wherein the product of the enzymatic activity is hydrogen peroxide.

132. The method of claim 130 wherein the indicator enzyme is a peroxidase.

133. The method of claim 132, wherein the peroxidase is selected from the group consisting of horseradish peroxidase, soybean peroxidase, haloperoxidase, myeloperoxidase, cytochrome c peroxidase, tulip peroxidase, lignin peroxidase, carrot peroxidase, peanut peroxidase, and peroxidase Novozyme® 502.

134. The method of claim 132, wherein the peroxidase is horseradish peroxidase.

135. The method of claim 132, wherein the peroxidase is soybean peroxidase.

136. The method of claim 130, wherein the reaction product is not a substrate for the indicator enzyme.

137. A method for imaging and analyzing microcolonies of cells, including the steps of:
forming in excess of 100 regions, each region including at least one biological cell on a substantially continuous base at an average density of at least about 10 regions per square centimeter;
initiating a chemical reaction in such regions that results in an optically detectable signal that changes over time, wherein at least one of the reactants participating in the chemical reaction has a molecular weight of at least about 1,000 daltons;
automatically optically monitoring each region over time for changes in the optical signal of portions of such regions; and
indicating which of such portions have a desired change in optical signal.

138. A method for imaging and analyzing microcolonies of cells, including the steps of:
forming in excess of 100 regions, each region including at least one biological cell on a substantially continuous base at an average density of at least about 10 regions per square centimeter;
initiating a chemical reaction in such regions that results in an optically detectable signal that changes over time, wherein at least one of the reactants participating in the chemical reaction has a molecular weight of at least about 10,000 daltons;
automatically optically monitoring each region over time for changes in the optical signal of portions of such regions; and
indicating which of such portions have a desired change in optical signal.

139. A method for imaging and analyzing microcolonies of cells, including the steps of:
forming in excess of 100 regions, each region including at least one biological cell on a substantially continuous base at an average density of at least about 10 regions per square centimeter;
initiating a chemical reaction in such regions that results in an optically detectable signal that changes over time, wherein at least one of the reactants participating in the chemical reaction has a molecular weight of at least about 100,000 daltons;
automatically optically monitoring each region over time for changes in the optical signal of portions of such regions; and
indicating which of such portions have a desired change in optical signal.

140. A method for imaging and analyzing microcolonies of cells, including the steps of:
forming in excess of 100 regions, each region including at least one biological cell on a substantially continuous base at an average density of at least about 10 regions per square centimeter;
initiating a chemical reaction in such regions that generates a reaction product and results in an optically detectable signal that changes over time, wherein the signal arises through the action of an indicator enzyme that converts the reaction product into optically detectable product;
automatically optically monitoring each region over time for changes in the optical signal of portions of such regions; and indicating which of such portions have a desired change in optical signal.

141. The method of claim 140, wherein the reactants comprise at least any one of the following: napthalene, 3-phenylpropionate, benzene, toluene, benzoic acid, anthracene, benzphetamine or coumarin.

142. The method of claim 140, wherein the chemical reaction comprises the use of an oxygenase enzyme.

143. The method of claim 142, wherein the oxygenase enzyme is selected from the group consisting of chloroperoxidase, cytochrome P450, methane monooxygenase, toluene monooxygenase, toluene dioxygenase, biphenyl dioxygenase and napthalene dioxygenase.

144. The method of claim 140, wherein the indicator enzyme is a peroxidase.

145. The method of claim 144, wherein the peroxidase is selected from the group consisting of horseradish peroxidase, cytochrome c peroxidase, tulip peroxidase, lignin peroxidase, carrot peroxidase, peanut peroxidase, soybean peroxidase, and peroxidase Novozyme® 502.

146. The method of claim 140, wherein the indicator enzyme is a laccase.

147. A method for imaging and analyzing microcolonies of cells, including the steps of:
    forming in excess of 100 regions, each region including at least one biological cell on a substantially continuous base at an average density of at least about 10 regions per square centimeter, wherein region formation includes the step of applying an inoculum to the substantially continuous base;
    initiating a chemical reaction in such regions that results in an optically detectable signal that changes over time;
    automatically optically monitoring each region over time for changes in the optical signal of portions of such regions; and
    indicating which of such portions have a desired change in optical signal.

148. The method of claim 147, wherein the inoculum application step comprises the use of vacuum filtration.

149. The method of claim 147, wherein the inoculum application step comprises the use of beads.

150. The method of claim 147, wherein the inoculum application step comprises aerosolization of the inoculum.

151. The method of claim 147 wherein the inoculum application step comprises the use of a spreader.

152. A method for imaging and analyzing microcolonies of cells, including the steps of:
    forming in excess of 100 regions, each region including at least one biological cell on a substantially continuous base at an average density of at least about 10 regions per square centimeter;
    initiating a chemical reaction in such regions that results in an optically detectable signal that changes over time, wherein the initiating comprises the use of a wick;
    automatically optically monitoring each region over time for changes in the optical signal of portions of such regions; and
    indicating which of such portions have a desired change in optical signal.

153. The method of claim 152, wherein the wick comprises a freely diffusible reactant.

154. The method of claim 152, wherein the wick is a gel.

155. The method of claim 154, wherein the gel comprises agarose.

156. The method of claim 154, wherein the gel comprises polyacrylamide.

157. The method of claim 152, wherein the wick comprises a polymer.

158. The method of claim 157, wherein the wick comprises cellulose.

159. The method of claim 157, wherein the wick comprises starch.

160. The method of claim 157, wherein the wick comprises xylan.

161. The method of claim 157, wherein the wick comprises guar.

162. The method of claim 157, wherein the wick comprises chitin.

163. The method of claim 157, wherein the wick comprises locust bean gum.

164. The method of claim 157, wherein the wick comprises pectin.

165. The method of claim 152, wherein the wick comprises paper.

166. The method of claim 152, wherein the wick comprises a non-freely diffusible reactant.

167. The method of claim 166, wherein the wick comprises a dye.

168. The method of claim 166, wherein the non-freely diffusible reactant comprises a polymer.

169. The method of claim 168, wherein the polymer is selected from the group consisting of agarose, starch, cellulose, xylan, guar chitin, locust bean gum and pectin.

170. An instrument for imaging and analyzing microcolonies of cells on a target, including:
    a light source for controllably emitting light having a selected set of wavelengths;
    a camera for controllably imaging light received from the target within a selected set of wavelengths;
    a sampling mechanism for controllably selecting samples from the target;
    a processor, coupled to the light source, the camera, and the sampling mechanism, for controlling the wavelengths of light emitted from the light source, the wavelengths of light imaged by the camera, and operation of the sampling mechanism; wherein the instrument automatically images regions of the target over time for changes in rate in any optical signal of portions of such regions, and automatically indicates which of such portions have a desired change over time in optical signal, wherein the instrument further comprises a diffuser interposed between the light source and the target for dispersing the emitted light to uniformly illuminate the target.

171. An instrument for imaging and analyzing microcolonies of cells on a target, including:
    a light source for controllably emitting light having a selected set of wavelengths;
    a camera for controllably imaging light received from the target within a selected set of wavelengths;
    a sampling mechanism for controllably selecting samples from the target;
    a processor, coupled to the light source, the camera, and the sampling mechanism, for controlling the wavelengths of light emitted from the light source, the wavelengths of light imaged by the camera, and operation of the sampling mechanism; wherein the instrument automatically images regions of the target over time for changes in rate in any optical signal of portions of such regions, and automatically indicates which of such portions have a desired change over time in optical signal, wherein the instrument further comprises a folded light path between the light source and the camera.

172. An instrument for imaging and analyzing microcolonies of cells on a target, including:
- a light source for controllably emitting light having a selected set of wavelengths;
- a camera for controllably imaging light received from the target within a selected set of wavelengths;
- a sampling mechanism for controllably selecting samples from the target;
- a processor, coupled to the light source, the camera, and the sampling mechanism, for controlling the wavelengths of light emitted from the light source, the wavelengths of light imaged by the camera, and operation of the sampling mechanism; wherein the instrument automatically images regions of the target over time for changes in rate in any optical signal of portions of such regions, and automatically indicates which of such portions have a desired change over time in optical signal, wherein the instrument further comprises a temperature-controlled forced-air heating system for maintaining the temperature of the microcolonies of cells on the target.

173. A method of performing solid-phase directed evolution enzyme screening, including the steps of:
- generating an average density of at least 10 microcolonies of cells per square centimeter on a solid phase, wherein a plurality of microcolonies express variants of at least one enzyme, wherein the method used to generate the variants is rational design;
- contacting the expressed variants with at least one optical signal substrate, each indicative of a desired enzymatic activity; and
- automatically detecting changes over time in one or more optical signals generated by one or more optical signal substrates in the microcolonies, wherein such changes indicate desired enzymatic activity of the variants of the enzyme.

174. The method of claim 173, wherein rational design includes the step of searching sequence space using protein design automation.

175. A method of performing solid-phase directed evolution enzyme screening, including the steps of:
- generating an average density of at least 10 microcolonies of cells per square centimeter on a solid phase, wherein a plurality of microcolonies express variants of at least one enzyme; wherein the method used to generate the variants is at least one selected from the group consisting of error-prone PCR, chemical mutagenesis, cassette/cartridge mutagenesis, mutator strain induced mutagenesis, recursive ensemble mutagenesis, exponential ensemble mutagenesis, DNA shuffling, and sequential random mutagenesis,
- contacting the expressed variants with at least one optical signal substrate, each indicative of a desired enzymatic activity; and
- automatically detecting changes over time in one or more optical signals generated by one or more optical signal substrates in the microcolonies, wherein such changes indicate desired enzymatic activity of the variants of the enzyme.

* * * * *